United States Patent [19]

Rosiak et al.

[11] Patent Number: 4,871,490
[45] Date of Patent: Oct. 3, 1989

[54] METHOD OF MANUFACTURING HYDROGEL DRESSINGS

[75] Inventors: Janusz Rosiak; Anna Ruci ska-Rybus, both of Piotrkowska; Wladyslaw Pekala, Laczna, all of Poland

[73] Assignee: Politechnika Lodzka, Lodz, Ul. Zwirki, Poland

[21] Appl. No.: 140,150

[22] Filed: Dec. 30, 1987

[30] Foreign Application Priority Data

Dec. 30, 1986 [PL] Poland .................................. 263410

[51] Int. Cl.[4] ............................................ B29C 35/08
[52] U.S. Cl. ..................................... 264/22; 128/156; 264/41; 264/233; 264/344
[58] Field of Search ..................... 264/22, 1.4, 41, 233, 264/344; 128/156

[56] References Cited

U.S. PATENT DOCUMENTS

| | | | |
|---|---|---|---|
| 3,426,754 | 2/1969 | Bierenbaum et al. | 264/41 |
| 3,496,254 | 2/1970 | Wichterle | 264/233 |
| 3,822,196 | 7/1974 | O'Driscoll et al. | 264/1.4 |
| 3,841,985 | 10/1974 | O'Driscoll et al. | 264/1.4 |
| 4,073,577 | 2/1978 | Höfer | 264/1.4 |
| 4,076,673 | 2/1978 | Burkholder, Jr. | 264/344 |
| 4,599,209 | 7/1986 | Dautzenberg et al. | 264/233 |

FOREIGN PATENT DOCUMENTS 2725261 of 0000 Fed. Rep. of Germany .
118053 of 0000 Poland .

OTHER PUBLICATIONS

Report of preliminary patent investigations of the invention–1986.

*Primary Examiner*—Jeffery Thurlow
*Attorney, Agent, or Firm*—Ladas & Parry

[57] ABSTRACT

A method of manufacturing hydrogel dressings from synthetic and natural polymers by polymerization and cross-linking involves pouring aqueous solutions of synthetic polymers, such as polyacrylamide and polyvinylpyrolidone, their monomers or their mixtures, natural polymers, such as gelatine or agar, or their mixtures and, possibly, plasticizing agents, such as poly/ethylene glycol/, poly/propylene glycol/ and silicone oils, of the following composition: 2–20 percent by weight of synthetic polymers, not more than 5 percent by weight of natural polymers, not less than 75 percent by weight of distilled water and 1–3 percent by weight of plasticizing agent, into a mould imparting a shape to the dressing, tightly closing in that mould and subjecting to an ionizing radiation dose not smaller than 25 kGy.

1 Claim, No Drawings

METHOD OF MANUFACTURING HYDROGEL DRESSINGS

The subject of this present invention is a method of manufacturing hydrogel dressings.

A method is known for manufacturing dressings in the form of biological gels, involving making a water suspension of gelatine, a natural polymer additionally containing pectins, bactericidal substances, salts of divalent iron and, possibly, carboxymethylcellulose and polyisobutylene and subjected to sterilisation.

The dressings obtained by this method have the form of a paste and must be applied to a wound in the form of a layer being 3 cm thick at least, they being used almost entirely for the therapy of mild burns.

Methods are also known for manufacturing hydrogel dressings, involving polymerising and crosslinking polyacrylamide, a synthetic polymer, or its mixture with a natural polymer, followed by conditioning and sterilising.

The disadvantage of the above-mentioned methods is the need for removing catalysts, initiators and unused reagents of the polymerising and chemical crosslinking process from such dressings, which is a complicated and labour-consuming operation. A method is also known from Polish Patent Specification No. 128,392 for manufacturing dressings including drugs, involving applying a layer of a hydrophilic gel obtained by the radiation polymerisation of synthetic polymers, such as polyacrylamide, polyvinylpyrrolidone, polyvinyl alcohol, polyethylene oxide, their monomers or their mixtures on the mechanical base of a dressing after or before impregnating it with a drug, whereafter the dressing is dried and sterilised. Although these dressings are characterised by a relatively long drug releasing time and the gel used to obtain them does not contain admixtures of any catalysts nor chemical substances, but they do not provide sufficient protection against a loss of water and penetration of bacteria to the wound, are opaque which prevents the observation of the wound healing process and, besides, the process of their manufacture is long and complicated.

The method of manufacturing hydrogel dressings from synthetic and natural polymers by polymerisation and cross-linking according to this present invention consists in pouring aqueous solutions of synthetic polymers, such as polyacrylamide, polyvinylpyrrolidone, their monomers or their mixtures, natural polymers, such as gelatine or agar, or their mixtures and, possibly, plasticising agents, such as poly/ethylene glycol/, poly/propylene glycol/, silicone oils, of the per cent by weight composition of 2-20 per cent of synthetic polymers, not more than 5 per cent of natural polymers, not less than 75 per cent of distilled water and 1-3 per cent of plasticising agent, into a mould imparting a shape to the dressing, is tighly closed in that mould and is subjected to a dose of ionising radiation in the range of 25-40 kGy.

The dressings obtained by the method as per this present invention find their application to dressing any kind of wounds, feature high flexibility, sufficiently high adhesion to skin and transperency thanks to which they prevent bacteria from penetrating to the wounds, enable the observation of the wound healing process and prevent water loss.

The method as per this present invention eliminates the dressing stabilisation process since that of obtaining and sterilising the dressing takes place during one common irradiation operation. The method as per this present invention also eliminates the operation of cleaning the gel of the admixtures of catalysts and chemical substances.

The method as per this present invention is disclosed in more detail by the examples provided below and not restricting its range of application.

Example I

An aqueous solution has been made up of acrylamide, polyvinylpyrrolidone, gelatine and agar, having the following composition: 10 parts by weight of acrylamide, 5 parts by weight of polyvinylpyrrolidone, 2 parts by weight of gelatine, 1 part by weight of agar and 82 parts by weight of distilled water. Such an amount of the solution has been poured into a Petri dish that a liquid layer of a thickness of 4 mm should be formed, said layer being on cooling wrapped into polyethylene film. After the edges of the film have been heat-sealed, the whole has been subjected to a gamma radiation dose of 30 kGy. The dressing thus obtained was fully sterile, elastic and transparent and very well adherred to the healthy skin and wound, providing a barrier to bacteria and preventing water loss.

Example II

An aqueous solution has been made up of vinylpyrolidone, poly/ethylene glycol/ and agar, having the following composition: 10 parts by weight of vinylpyrolidone, 1.5 parts by weight of poly/ethylene glycol/, 1.5 parts by weight of agar and 87 parts by weight of distilled water. The further procedure was identical to that of Example I.

The dressing showed the properties analogous to those of the dressing obtained in Example I.

Example III

An aqueous solution has been made up of polyvinylpyrolidone, poly/ethylene glycol/, agar and sodium chloride, having the following composition: 5 parts by weight of polyvinylpyrolidone, 1.5 parts by weight of poly/ethylene glycol/, 1.5 parts by weight of agar, 0.9 part by weight of sodium chloride and 91.1 parts by weight of distilled water.

The further procedure was identical to that of Example I and a gamma radiation dose of 35 kGy was used.

The dressing thus obtained showed the properties analogous to those of the dressing obtained in Example I. Irradiation with electron beam was found effective.

Example IV

An aqueous solution has been made up of polyacrylamide and agar, having the following composition: 2.5 parts by weight of polycrylamide, 1.5 parts by weight of agar and 96 parts by weight of distilled water.

The further procedure was identical to that of Example I and a gamma radiation dose of 40 kGy was used.

The dressing thus obtained showed the properties analogous to those of the dressing obtained in Example I.

I claim:

1. A method of manufacturing hydrogel dressings from polymers by radiation cross-linking, comprising an aqueous solution containing 2-10 per cent by weight of polyvinylpyrrolidone, no more than 3 percent by weight of agar and 1-3 percent by weight of poly(ethylene) glycol; pouring the solution into a mould to shape the dressing; tightly closing the mould and subjecting the mould to an ionizing radiation dose in the range of 25-40 KGy.

* * * * *